United States Patent [19]

Sakito et al.

[11] Patent Number: 5,145,998
[45] Date of Patent: Sep. 8, 1992

[54] METHOD FOR PRODUCING OPTICALLY ACTIVE AMINES

[75] Inventors: Yoji Sakito, Takarazuka; Gohfu Suzukamo, Ibaraki; Yukio Yoneyoshi, Otsu, all of Japan

[73] Assignee: Sumitomo Chemical Company, Limited, Osaka, Japan

[21] Appl. No.: 593,384

[22] Filed: Oct. 2, 1990

Related U.S. Application Data

[63] Continuation of Ser. No. 284,817, Dec. 14, 1988, abandoned, which is a continuation of Ser. No. 21,501, Mar. 4, 1987, abandoned.

[30] Foreign Application Priority Data

Mar. 14, 1986 [JP] Japan .................................. 61-57926
Jun. 10, 1986 [JP] Japan ................................ 61-134003

[51] Int. Cl.$^5$ .................. C07C 209/40; C07C 249/04; C07B 57/00; C07F 5/02
[52] U.S. Cl. ..................... 564/321; 564/256; 564/303; 564/364; 564/373; 564/9; 564/385; 564/489; 564/415
[58] Field of Search ............... 564/256, 303, 304, 373, 564/9, 321, 385, 489, 415

[56] References Cited

U.S. PATENT DOCUMENTS

| | | | |
|---|---|---|---|
| 3,597,458 | 8/1971 | Nakamura et al. | 564/373 X |
| 3,739,019 | 6/1973 | Ueda et al. | 564/373 X |
| 3,839,441 | 10/1974 | Hellerbach | 564/304 |
| 3,976,696 | 8/1976 | Freed et al. | 564/375 |
| 4,536,599 | 8/1985 | Masuko et al. | 564/373 X |
| 4,749,809 | 6/1988 | Yoneyoshi et al. | 548/262 |
| 4,760,149 | 7/1988 | Yoneyoshi et al. | 548/262 |

OTHER PUBLICATIONS

Landor, "A Segmetric Syntheses . . . " J. Chem. Soc., Perkin Trans I, 1902–1904 (1974).
Itsuno, "Asymetric Syntheses . . . " J. Chem. Soc., Perkin Trans I, 2039–2044 (1985).
Tetrahedron Letters, vol. 24, No. 8, 1983, pp. 759–760; F. Santiesteban et al.
Chemical Abstracts, vol. 78, No. 20, 1973, p. 447, col. 2, Abstract No. 124165n.
Patent Abstracts of Japan, vol. 11, No. 8 (C-396)[2455], 9 Jan. 1987 (JP 61-186,350).
Patent Abstract of Japan, vol. 10, No. 172 (C-354)[2228], 18 Jun. 1986 (JP 61-22,091).
Patent Abstracts of Japan, vol. 10, No. 166 (C-353)[2222], 13 Jun. 1986 (JP 61-18,790).

*Primary Examiner*—Marianne M. Cintins
*Assistant Examiner*—Michael B. Hydorn
*Attorney, Agent, or Firm*—Stevens, Davis, Miller & Mosher

[57] ABSTRACT

A method for producing an optically active amine which is an important compound as a resolving agent for medicines, agricultural chemicals, intermediates thereof, etc is disclosed.

4 Claims, No Drawings

METHOD FOR PRODUCING OPTICALLY ACTIVE AMINES

This application is a Continuation of application Ser. No. 07/284,817, filed Dec. 14, 1988, now abandoned which in turn is a Continuation of application Ser. No. 07/021,501, filed Mar. 4, 1987, now abandondoned.

The present invention relates to a method for producing optically active amines, and more particularly, it relates to a method for producing optically active amines represented by the general formula (III),

wherein $R_6$ and $R_7$, which are different from each other, represent an aryl group which may be substituted with an alkyl group, an aralkyl group which may be substituted with an alkyl group, or an alkyl group, and * represents an asymmetric carbon atom.

The optically active amines represented by the general formula (III) are an important compound as a resolving agent for medicines, agricultural chemicals, intermediates thereof, etc. It is also well known that said amines are produced by once producing their racemate which is then optically resolved with an optically active acid, etc. (for example, refer to Optical Resolution Procedure for Chemical Compounds, Vol. 1).

The conventional method of producing optically active amines by optical resolution is a method of once producing the racemate, forming its salt by reaction with an optically active acid, crystallizing one of the resulting diastereomer salts by making use of a difference in solubility between the salts, separating the crystallized salt, decomposing the salt by reaction with an alkali and separating and recovering the optically active amine which is one of enantiomers. This method, however, has a defect that the operation is troublesome with low efficiency.

On the other hand, a method of synthesizing optically active amines by the asymmetric reduction of the oxime of asymmetric ketones (e.g. acetophenone) has been tried. For example, a method using asymmetric reducing agents obtained from optically active glucofuranoses and lithium aluminum hydride is reported in J. Chem. Soc., Perkin I, 1902 (1974), and a method using asymmetric reducing agents obtained from optically active α,α-diphenyl-β-aminoalcohols and a boron hydride compound is reported in J. Chem. Soc., Perkin I, 2039 (1985).

However, the former method has a problem that the optical yield is low, and the latter method has problems that access to the asymmetric assistants, i.e. optically active α,α-diphenyl-β-aminoalcohols, is not always easy industrially, and besides that, for producing optically active amines having different absolute steric configurations R and S, asymmetric assistants having the corresponding absolute steric configurations are considered to be necessary, so that two kinds of optically active α,α-diphenyl-β-aminoalcohol having different absolute steric configurations, R and S, should be always ready for use.

In order to solve the above problems, the present inventors extensively studied a method of producing optically active amines by the asymmetric reduction of the oxime of asymmetric ketones, and as a result, found that even optically active α-phenyl-β-aminoalcohols having a simple structure are effective as asymmetric assistant and yet they are easily available industrially, and that reducing agents obtained from said aminoalcohols and a boron hydride compound give optically active amines easily and in high optical yields. Further, the present inventors found that any of R- and S-optically active amines can freely be produced using either one of the R- or S-asymmetric assistant.

The present invention provides a method for producing an optically active amine represented by the general formula (III),

wherein $R_6$ and $R_7$, which are different from each other, represent an aryl group which may be substituted with an alkyl group, an aralkyl group which may be substituted with an alkyl group, or an alkyl group, and * represents an asymmetric carbon atom, characterized by reacting an asymmetric reducing agent obtained from an optical active aminoalcohol represented by the general formula (I),

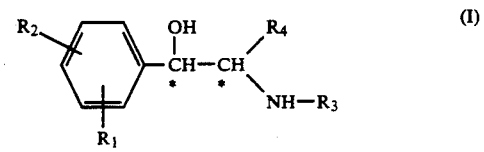

wherein $R_1$ and $R_2$ represent a hydrogen atom or an alkyl or alkoxyl group, $R_3$ represents a hydrogen atom or an alkyl group, $R_4$ represents an alkyl group, and * is as defined above, and a boron hydride compound with the anti-form or syn-form isomer of oxime derivatives represented by the general formula (II),

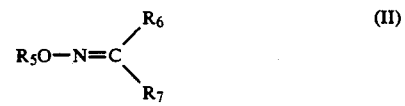

wherein $R_5$ represents an alkyl, aralkyl or alkyl-substituted silyl group, and $R_6$ and $R_7$ are as defined above, or a mixture of the isomers which is rich in either one of them, said optically active amine represented by the general formula (III) having an absolute steric configuration which is the same as that of the amino group-substituted carbon atom in the general formula (I) when the oxime derivative of the general formula (II) is of the anti-form structure or rich in the same and opposite to that of the amino group-substituted carbon atom in the general formula (I) when the oxime derivative of the general formula (II) is of the syn-form structure or rich in the same.

The present invention will be illustrated below in detail.

The optically active aminoalcohols used in the present invention are represented by the general formula (I), and substituents, $R_1$ and $R_2$, at the benzene ring include for example a hydrogen atom, lower alkyl groups (e.g. methyl, ethyl, propyl, butyl, pentyl, hexyl) and lower alkoxy groups (e.g. methoxy, ethoxy, propoxy, butoxy, pentyloxy, hexyloxy), their positions being not particularly limited.

A substituent $R_3$ includes for example a hydrogen atom and lower alkyl groups (e.g. methyl, ethyl, propyl, butyl, pentyl, hexyl), and a substituent $R_4$ includes for example lower alkyl groups (e.g. methyl, ethyl, propyl, butyl, pentyl, hexyl). More specifically, for example the following compounds can be given as said optically active aminoalcohols.

Norephedrine
Ephedrine
2-Amino-1-(2-methylphenyl)-1-propanol
2-Amino-1-(2-ethylphenyl)-1-propanol
2-Amino-1-(2-methoxyphenyl)-1-propanol
2-Amino-1-(2-ethoxyphenyl)-1-propanol
2-Amino-1-(2,5-dimethylphenyl)-1-pronanol
2-Amino-1-(2,5-diethylphenyl)-1-propanol
2-Amino-1-(2,5-dimethoxyphenyl)-1-propanol
2-Amino-1-(2,5-diethoxyphenyl)-1-propanol
2-Amino-1-(2-methoxy-5-methylphenyl)-1-propanol
2-Amino-1-phenyl-1-butanol
2-Amino-1-(2-methylphenyl)-1-butanol
2-Amino-1-(2-ethylphenyl)-1-butanol
2-Amino-1-(2-methoxyphenyl)-1-butanol
2-Amino-1-(2-ethoxyphenyl)-1-butanol
2-Amino-1-(2,5-dimethylphenyl)-1-butanol
2-Amino-1-(2,5-diethylphenyl)-1-butanol
2-Amino-1-(2,5-dimethoxyphenyl)-1-butanol
2-Amino-1-(2,5-diethoxyphenyl)-1-butanol
2-Amino-1-(2-methoxy-5-methylphenyl)-1-butanol
2-Amino-1-phenyl-1-pentanol
2-Amino-1-(2,5-dimethylphenyl)-1-pentanol
2-Amino-1-(2,5-dimethoxyphenyl)-1-pentanol
2-Amino-1-phenyl-1-hexanol
2-Amino-1-phenyl-1-heptanol
2-Amino-1-phenyl-1-octanol, etc.

The present invention uses asymmetric reducing agents obtained from the optically active aminoalcohols (I) as described above and a boron hydride compound. The boron hydride compound includes for example alkali metal borohydrides such as lithium borohydride, sodium borohydride, etc., and boranes such as diborane, borane dimethyl sulfide complex, borane.tetrahydrofuran complex, etc. The amount of the boron hydride compound used is generally from 1 to 4 times by mole, preferably from 2 to 3 times by mole based on the optically active aminoalcohol (I).

In preparing the asymmetric reducing agents, there are generally used solvents such as ethers (e.g. diethyl ether, tetrahydrofuran, dioxane, diglyme), hydrocarbons (e.g. benzene, toluene, xylene), halogenated hydrocarbons (e.g. chlorobenzene, chloroform, 1,2-dichloroethane) and mixtures thereof.

When alkali metal borohydrides are used as the boron hydride compound, the asymmetric reducing agents are generally prepared by suspending or dissolving an alkali metal borohydride in an optically active aminoalcohol (I) solution and adding a mineral acid (e.g. hydrochloric acid) or Lewis acid (e.g. boron fluoride, boron chloride). The amount of the acid is generally from 0.8 to 2 times by mole, preferably from 0.9 to 1.5 times by mole based on the alkali metal borohydride.

When boranes are used as the boron hydride compound, the asymmetric reducing agents are prepared by adding a borane to an optically active aminoalcohol (I) solution. The preparation temperature is generally 100° C. or lower, preferably 20° C. or lower independently of the kind of the boron hydride compounds.

The present invention is characterized by reacting the asymmetric reducing agent thus obtained with the anti-form or syn-form isomer of oxime derivatives represented by the foregoing formula (II) or a mixture of the isomers which is rich in either one of them. A substituent $R_5$ in the oxime derivatives include for example $C_1$–$C_{10}$ alkyl groups (e.g. methyl, ethyl, propyl, butyl, pentyl, cyclopentyl, hexyl, cyclohexyl, heptyl, cycloheptyl, octyl, cyclooctyl, nonyl, decyl), $C_7$–$C_{11}$ aralkyl groups (e.g. benzyl, $\beta$-phenetyl, naphthylmethyl) and $C_3$–$C_{12}$ alkylsilyl groups (e.g. trimethylsilyl, dimethyl-tert-butylsilyl, tri-n-propylsilyl, tri-n-butylsilyl).

Substituents $R_6$ and $R_7$ include for example aryl and alkyl-substituted aryl groups (e.g. phenyl, o-, m- or p-methylphenyl, o-, m- or p-ethylphenyl, o-, m- or p-propylphenyl, 2,3-, 2,4-, 2,5- or 2,6-dimethylphenyl, $\alpha$ or $\beta$-naphthyl, lower alkyl groups (e.g. methyl, ethyl, propyl, butyl, pentyl, cyclopentyl, hexyl, cyclohexyl) and aralkyl and alkyl-substituted aralkyl groups [e.g. benzyl, o-, m- or p-tolylmethyl, (o-, m- or p-ethylphenyl)-methyl, (2,3-, 2,4-, 2,5- or 2,6-dimethylphenyl)-methyl, 2-phenylethyl, 2-(o-, m- or p-tolyl)ethyl, (2,3-, 2,4-, 2,5- or 2,6-dimethylphenyl)ethyl, 3-phenylpropyl].

More specifically, there are given for example the syn-form and anti-form isomers of O-methyloxime, O-octyloxime, O-cyclohexyloxime, O-benzyloxime, O-trimethylsilyloxime, etc. of the following compounds:
Acetophenone, propiophenone, butyrophenone, isobutyrophenone, $\alpha$-acetonaphthone, $\beta$-acetonaphthone, phenyl benzyl ketone, phenyl p-tolylmethyl ketone, phenyl m-tolylmethyl ketone, phenyl o-tolylmethyl ketone, phenyl 2-phenylethyl ketone, 2-butanone, 2-pentanone, 2-hexanone, 3-hexanone, 2-heptanone, 3-heptanone, 3-octanone, cyclohexyl methyl ketone, cyclohexyl ethyl ketone, $\alpha$-phenylacetone, 2-phenylethyl methyl ketone, 2-phenylethyl ethyl ketone, 3-phenylpropyl methyl ketone, etc.; and a mixture of the isomers which is rich in either one of them.

These ketoximes can easily be produced from the corresponding ketones by the well-known method. Also, when only one of the syn-form and anti-form isomers of the ketoximes is used, the other isomer which remains after separation can be converted to a required isomer by the well-known syn/anti isomerization, so that the ketoximes which are a material can be used effectively.

Solvents used in reacting the oximes (II) with the foregoing reducing agents include ethers (e.g. diethyl ether, tetrahydrofuran), hydrocarbons (e.g. benzene, toluene, xylene), halogenated hydrocarbons (e.g. chlorobenzene, chloroform, 1,2-dichloroethane) and mixtures thereof. The amount of the solvent used is generally from 2 to 50 times by weight based on the oximes (II). The amount of the reducing agents used is generally from 1 to 6 times by mole, preferably from 1 to 3 times by mole, as converted to the optically active aminoalcohol (I), based on the oximes (II). The reaction temperature is generally 100° C. or lower, preferably from $-20°$ to 40° C.

The progress of the reaction can be followed by analytical means such as gas chromatography, etc.

After completion of the reaction, by adding a mineral acid (e.g. hydrochloric acid) to the reaction solution to quench the reducing agent, making the solution alkaline with caustic soda, etc. and extracting the solution with a solvent (e.g. toluene), the desired optically active amines (III) and optically active aminoalcohols (I) used as an asymmetric assistant can be obtained. Thereafter, by separating the both from each other by the usual separation techniques such as distillation, etc., the desired compounds can be obtained.

Hereupon, when a substituent $R_7$ in the general formula (III) representing the optically active amines is an aralkyl group and $R_6$ is an aryl group, the desired product (III) and the asymmetric assistant (I) can easily be separated and recovered separately and successively by merely changing the pH of the extract. For example, by adjusting the pH of the extract to from 8.5 to 9.5, the desired product (III) can first be recovered selectively and then by changing the pH to 11 or more, the asymmetric assistant (III) can be recovered selectively.

Also, by using hexane, etc. as extraction solvent and making use of a difference in solubility between the product (III) and the asymmetric assistant (I), the product (III) can be recovered selectively from the reaction mass made alkaline.

The product (III) obtained by the method described above can further be purified by means such as distillation, column chromatography, etc.

Thus, the desired optically active amines (III) can be produced, and according to the method of the present invention, any of R- and S-optically active amines can freely be produced by merely using either one of the R- or S-asymmetric assistant. For example, when R-optically active amines need to be produced using the R-asymmetric assistant, they can be obtained by using the anti-form oxime ether. While when S-optically active amines need to be produced using the same asymmetric assistant, they can be obtained by using the syn-form oxime ether.

Also, according to the method of the present invention, by using the R- and S-asymmetric assistants, any of R- or S-optically active amines can be obtained from both of the anti-form and syn-form oxime ether. For example, when R-optically active amines are required, they can easily be obtained by combining the anti-form oxime ether with the R-asymmetric assistant, and the syn-form oxime ether with the S-asymmetric assistant.

In addition to the advantages described above, the present invention have advantages that the optical yield of the desired products is high, and that the asymmetric ligand used is easily available.

The present invention will be illustrated in detail with reference to the following examples, but it is not limited to these examples.

EXAMPLE 1

A solution of 70 mg (0.33 mmole) of erythro-(−)-2-amino-1-(2,5-dimethoxyphenyl)-1-propanol in tetrahydrofuran (THF) was cooled to −70° C., and after adding dropwise a THF solution of 0.66 mmole of borane, the temperature was gradually raised to room temperature.

A THF solution of 50.2 mg (0.21 mmole) of anti-form phenyl p-tolylmethyl ketone O-methyloxime was then added dropwise thereto, and after stirring at room temperature for 12 hours, the temperature was raised to 60° C., followed by stirring at the same temperature for 5 hours.

Thereafter, 18% hydrochloric acid was added, and after stirring at the same temperature for 1 hour, the reaction solution was concentrated under reduced pressure. The residue was made alkaline with addition of an aqueous caustic soda solution and extracted with toluene, and the resulting organic layer was concentrated and purified by column chromatography on alumina to obtain an optically active 1-phenyl-2-(p-tolyl)ethylamine.

The optical purity was measured by liquid chromatography with an optically active column. As a result, it was found that the optical purity was 94%, the absolute steric configuration was S and the yield was 63%.

EXAMPLE 2

A THF solution of 1.26 g (8.3 mmoles) of (−)-norephedrine was cooled to −70° C., and after adding dropwise a THF solution of 16.6 mmoles of borane, the temperature was gradually raised to room temperature.

A THF solution of 0.67 g (2.8 mmoles) of anti-form phenyl p-tolylmethyl ketone O-methyloxime was then added dropwise thereto, and after stirring at room temperature for 12 hours, the temperature was raised to 60° C., followed by stirring at the same temperature for 5 hours.

Thereafter, 18% hydrochloric acid was added, and after stirring at the same temperature for 1 hour, the reaction solution was concentrated under reduced pressure. The residue was adjusted to a pH of 9.1 with addition of an aqueous caustic soda solution and extracted with toluene, and the resulting organic layer was concentrated to obtain an optically active 1-phenyl-2-(p-tolyl)ethylamine.

The optical yield was 94%, the absolute steric configuration was S and the yield was 61%.

EXAMPLE 3

A THF solution of 278 mg (1.84 mmoles) of (−)-norephedrine was cooled to −30° C. and after adding dropwise 4 mmoles of borane.dimethyl sulfide complex, the temperature was gradually raised to room temperature.

A THF solution of 183 mg of anti-form 2-acetonaphthone O-methyloxime was then added, and after stirring at room temperature for 20 hours, 5 mmoles of borane.dimethyl sulfide complex was added, followed by stirring at 60° C. for 5 hours. Thereafter, 18% hydrochloric acid was added, and after stirring at the same temperature for 1 hour, chloroform was added, followed by separating the aqueous layer from the organic layer.

the separated aqueous layer was made alkaline with addition of an aqueous sodium hydroxide solution and extracted with hexane, and the separated hexane layer was concentrated to obtain an optically active 1-(2-naphthyl)-ethylamine.

The optical yield was 92%, the absolute steric configuration was S and the yield was 73%.

EXAMPLE 4

Procedure was carried out int he same manner as in Example 2 except that 16.6 mmoles of borane.diemthyl sulfide complex was used in place of borane and 1,2-dichloroethane was used in place of THF, to obtain 1-phenyl-2-(p-tolyl)ethylamine.

The optical yield was 91%, the absolute steric configuration was S and the yield was 635.

EXAMPLES 5 to 13

Procedure was carried out using varying substrates, and the results are shown in Table 1. The procedure in Examples 5 to 8 was carried out according to Example 2, and that in Examples 9 to 13 was carried out according to Example 3.

TABLE 1

| Example No. | Substrate | Product | Optical purity (%) | Absolute steric configuration | Yield (%) |
| --- | --- | --- | --- | --- | --- |
| 5 | Anti-form phenyl p-tolylmethyl ketone O-octyloxime | 1-phenyl-2-(p-tolyl)ethylamine | 90 | S | 64 |
| 6 | Anti-form phenyl p-tolylmethyl ketone O-trimethylsilyloxime | The same as above | 91 | S | 63 |
| 7 | Anti-form phenyl p-tolylmethyl ketone O-benzyloxime | The same as above | 89 | S | 82 |
| 8 | Syn-form phenyl p-tolylmethyl ketone O-methyloxime | The same as above | 92 | R | 58 |
| 9 | Syn-form 2-acetonaphthone O-methyloxime | 1-(2-Naphthyl)-ethylamine | 80 | R | 73 |
| 10 | Anti-form 2-octanone O-benzyloxime | 2-Aminooctane | 80 | S | 65 |
| 11 | Syn-form 2-octanone O-benzyloxime | The same as above | 79 | R | 45 |
| 12 | Anti-form 4-phenyl-2-butanone O-methyloxime | 2-Amino-4-phenyl-butane | 86 | S | 40 |
| 13 | Syn-form 4-phenyl-2-butanone O-methyloxime | The same as above | 81 | R | 46 |

EXAMPLE 14

To a THF solution of 163 mg (1.08 mmole) of (-)-norephedrine was added 92 mg (2.43 mmoles) of sodium borohydride, and after cooling to $-65°$ C., 460 mg (3.24 mmoles) of boron trifluoride etherate was added dropwise thereto, and the temperature was raised to 20° C. over about 3 hours. Thereafter, a THF solution of 115 mg (0.48 mmole) of anti-form phenyl p-tolylmethyl ketone O-methyloxime was added dropwise, and after stirring at 20° C. for 12 hours, the temperature was raised to 60° C., followed by stirring at the same temperature for 5 hours.

Thereafter, 18% hydrochloric acid was added, and after stirring at the same temperature for 1 hour, the reaction solution was concentrated under reduced pressure. The residue was made alkaline with addition of an aqueous caustic soda solution and extracted with toluene. The organic layer obtained was concentrated and purified by column chromatography on alumina to obtain an optically active 1-phenyl-2-(p-tolyl)ethylamine.

The optical yield was 81%, the absolute steric configuration was S and the yield was 41%.

What is claimed is:

1. In a process for producing an optically active amine represented by the formula (III)

wherein $R_6$ and $R_7$, which are different from each other, represent $C_6-C_{10}$ aryl, alkyl substituted $C_6-C_{10}$ aryl, $C_7-C_{10}$ aralkyl, alkyl substituted $C_7-C_{10}$ aralkyl, or $C_1-C_6$ akyl and * represents an asymmetric carbon atom, by reaction an asymmetric reducing agent with an oxime derivative represented by the formula (II)

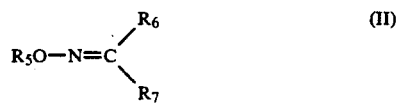

wherein $R_5$ represents $C_1-C_{10}$ alkyl, $C_7-C_{11}$ aralkyl or $C_3-C_{12}$ alkyl silyl, and $R_6$ and $R_7$ are as defined above, the improvement comprising reacting a boron hydride compound and an optically active aminoalcohol represented by the formula (I),

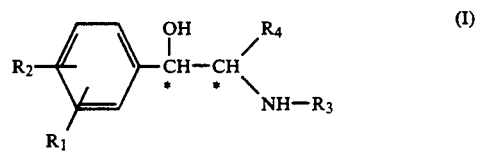

wherein $R_1$ and $R_2$ represent hydrogen, $C_1-C_6$ alkyl or $C_1-C_8$ alkoxyl, $R_3$ represents hydrogen or $C_1-C_6$ alkyl, $R_4$ represents $C_1-C_6$ alkyl, and * is as defined above, to produce said asymmetric reducing agent, and selecting the syn-form or a syn-form rich mixture of the oxime derivative of formula (II) for reaction with said reducing agent when the absolute steric configuration of the desired amine of formula (III) is opposite to the absolute steric configuration of the amino group-substituted atom int he aminoalcohol of formula (I), or alternatively selecting the anti-form or an anti-form rich mixture of the oxime derivative of formula (II) for reaction with said reducing agent when the absolute steric configuration of the desired a mine of the formula (III) is the same as that in the amino alcohol of formula (I).

2. The method for producing an optically active amine according to claim 1, wherein the boron hydride compound is selected from the group consisting of bore, borane dimethyl sulfide complex borane tetrahydrofuran complex.

3. The method for producing an optically active amine according to claim 1, wherein the boron hydride compound is an alkali metal borohydride.

4. The method for producing an optically active amine according to claim 1, wherein the boron hydride compound is present in an amount of 2 to 3 times by mole based on the optically active aminoalcohol f the formula (I).

* * * * *